(12) United States Patent
Watkins (10) Patent No.: US 7,267,437 B2
(45) Date of Patent: Sep. 11, 2007

(54) BIOMIMICKING APPLICATIONS OF HUMAN SENSORY SYSTEMS

(76) Inventor: Wendell Watkins, 3302 Gabel, El Paso, TX (US) 79904

( * ) Notice: Subject to any disclaimer, the term of this patent is extended or adjusted under 35 U.S.C. 154(b) by 479 days.

(21) Appl. No.: 10/621,334

(22) Filed: Jul. 18, 2003

(65) Prior Publication Data

US 2005/0012897 A1    Jan. 20, 2005

(51) Int. Cl.
 *A61B 3/00*    (2006.01)
(52) U.S. Cl. ............ 351/203; 351/201; 351/243; 351/246; 351/239; 351/240; 351/223
(58) Field of Classification Search ........ 351/200–247; 600/38, 558
See application file for complete search history.

(56) References Cited

U.S. PATENT DOCUMENTS

| | | | |
|---|---|---|---|
| 2,001,024 A | | 3/1934 | Idzal |
| 2,168,308 A * | | 8/1939 | Ames et al. ............... 351/201 |
| 4,405,920 A | | 9/1983 | Weisstein |
| 5,088,810 A | | 2/1992 | Galanter et al. |
| 5,363,154 A * | | 11/1994 | Galanter et al. ........... 351/203 |
| 5,555,324 A | | 9/1996 | Waxman et al. |
| H1599 H | | 10/1996 | Task et al. |
| 5,594,841 A * | | 1/1997 | Schutz ...................... 345/419 |
| 5,870,493 A | | 2/1999 | Vogl et al. |
| 5,963,247 A * | | 10/1999 | Banitt ...................... 348/121 |
| 6,081,753 A | | 6/2000 | Meitzler et al. |
| 6,121,969 A | | 9/2000 | Jain et al. |
| 6,213,956 B1 * | | 4/2001 | Lawton ..................... 600/558 |
| 6,333,757 B1 | | 12/2001 | Faris |
| 6,364,485 B1 * | | 4/2002 | Fateh ........................ 351/203 |
| 6,364,486 B1 | | 4/2002 | Ball et al. |
| 6,443,572 B1 | | 9/2002 | Lawson |
| 6,517,204 B1 * | | 2/2003 | Ghahramani ............ 351/201 |

FOREIGN PATENT DOCUMENTS

WO    WO0055830    9/2000

OTHER PUBLICATIONS

Shaywitz, Sally; "Overcoming Dyslexia," Random House, Inc., (Knopf), 2003.
Watkins, Wendell R.; "Biomimicking Applications of the Search and Target Acquisition, Recognition, and Identification Methods Used In Animal Binaural Vision;" U.S. Patent and TradeMark Office, Disclosure Document No. 518460; Sep. 19, 2002, Washington, D.C.
Lawson, Alison Marie; "Method and Apparatus For Treating Dyslexia," U.S. Pagent No. 6,443,572, Issued Sep. 3, 2003.
Hofer, Heidi and Williams, David R.; "The Eye's Mechanisms For Autocalibration," Optics And Photonics News, (pp. 34-39), Jan. 2002.
Watkins, W.R.; "Multispectral Image Processing: The Nature Factor," Series In Machine Perception and Artificial Intelligence; (vol. 44); J. Shen, P.S.P. Wang, T. Zhang (Eds.) Multispectral Image Prcessing And Pattern Recognition, World Scientific, New Jersey, (pp. 37-48), 2001.

(Continued)

*Primary Examiner*—Brian L. Casler
*Assistant Examiner*—Sanjay Cattungal
(74) *Attorney, Agent, or Firm*—R. Wayne Pritchard, P.E.

(57) ABSTRACT

A method of sensory training and testing systems focusing upon the development of pre-attentive and attentive vision for the enhancement of the individual's ability to perform specific functions.

18 Claims, 2 Drawing Sheets

OTHER PUBLICATIONS

Watkins, W.R., Heath, G.D., Phillips, M.D., Valeton, M. and Toet, A., "Search and Target Acquisition: Single Line Of Sight Versus Wide Baseline Stereo," Opt. Eng. 40(9) (pp. 1914-1927) 2001.

Rohde, B.L and Watkins, W., "Effect of Color Frequency Combinations and Noise on Depth Perception Using RGB Stereo Sensor Fusion," Proc. 9th Annual USARL/USMA Technical Symposium, http://www.dean.usma.edu/math/research/msce/9th_AUTS/default.htm, at APG Session 2000.

Watts, Robert G. and Bahill, A. Terry, "Keep Your Eyes On The Ball," W.H. Freeman and Co., New York, (pp. 171-209) 2000.

Watkins, W.R., CuGlock-Knopp, V.G., Jordan, J.B., Marinos, A.J., Phillips, M.D., and Merritt, J.O., "Sensor Fusion: A Preattentive Vision Approach," Proc. SPIE 4029 (pp. 59-67) 2000.

Ross, T.H, Watkins, W.R., Kobylski, O., and Heath, O., "Effect of Noise and Background on Depth Perception Using RGB Stereo Sensor Fusion," Proc. 8th Annual USARL/USMA Technical Symposium (pp. 97-103) 2000.

Ross, T.H., Watkins, Kobylski, G., and Heath, G., "Effect of Noise and Background on Depth Perception Using RGB Stereo Sensor Fusion," Proc 8th Annual USARL/USMA Technical Symposium (pp. 97-103) 2000.

Heath, G., Watkins, W.R., Phillips, M.D., "A Comparison Of Abserver Task Performance: Three Dimensional vs. Two Dimensional Displays," Proc. 8th Annual USARL/USMA Technical Symposium (pp. 199-214) 2000.

Marinos, A.J., Watkins, W.R., and Phillips, M.D., "Effect of RGB Stereo Sensor Fusion On Target And Range Identification," Proc. 7th Annual USARL/USMA Technical Symposium, (pp. 68-68), 1999.

Jain, Anil K.; "Fundamentals Of Image Processing," Englewood Cliffs, NJ, Prentice Hall, 1989.

Watkins, W.R., Jordan, J.B., and Trivedi, M.M.; "Novel Applications Of Hyperstereo Vision," Proc. SPIE 3110, (pp. 72-88); 1997.

Rosanes-Beret, M.B., "Do You Really Need Eyeglasses," New Hork, I.I., Inc. 1985.

Bereford, S.M., Muris, D.W., M.J.A..En, and young, f.a., Inprove Your vision Without Glasses Or Contact Lenses, Simon & Schuster (Fireside) New York, 1996.

Pettigrew, John D.; "The Neurophysiology Of Binocular Vision," Scientific American, (pp. 84-85), Aug. 1972.

Watts, Robert G., Bahill, Terry, W.H. Freeman and Company; Keep Your Eye On The Ball, 2000.

* cited by examiner

BIOMIMICKING APPLICATIONS OF HUMAN SENSORY SYSTEMS

BACKGROUND OF THE INVENTION

1. Field of the Invention

Reference is made to Disclosure Document Number 518,460, Watkins. The invention relates to human sensory training and testing systems. More particularly, the invention relates to sensory training and testing systems focusing upon the development of pre-attentive and attentive vision for the enhancement of the individual's ability to perform specific functions.

2. Description of the Prior Art

Imagine a situation where one of a person's senses, such as the vision from one eye, the hearing from an ear, the smell from a nose, the touch from one hand, has been impaired through damage to the nerves associated with such sense. What if the sense could be improved through use of the other unaffected senses. Imagine further a situation where one eye has better vision than the other. What if the eye with the better vision could be used to train the underperforming eye. The present invention relates to sensory training and testing systems focusing upon the development of the pre-attentive and attentive vision processes. To understand this method, one must first understand the concepts of pre-attentive and attentive vision.

Eagles have exceptionally good visual acuity being able to see a 10-cm long mouse body from a viewing height of hundreds of meters above the ground. This phenomenal vision is, however, constrained to a very small portion of their retina termed the fovea, which provides a detailed, but very limited, field of view. Humans have the same retinal configuration with a central fovea comprised of dense populations of three eye color cone sensors (red, green, and blue).

The eagle does not use its foveal vision to locate its prey though. The foveal vision has too small of a field of view and would be like looking at a large area picture through a soda straw. This task would be analogous to the "Where's Waldo" problem where there is just too much similar looking clutter in the scene to easily locate the one correct object.

Eagles and other binaural predators locate their prey through the use of depth and motion cues observed via the outer portion of retina, instead of trying to find a particular object in the large background terrain area. Motion and depth cues are basically mathematically indistinguishable because they represent a spatial shift of the object of interest against its background. For the case of the motion cues, the spatial shifts are caused by movement of the object against its background in time. With regard to the depth cues, the spatial shifts are a result of parallax between the lines of sight of the predator's two eyes. While for the eagle the dominant cue for looking down on a more or less flat surface is motion, for a lion looking out horizontally over the savanna for prey both motion and depth cues are important (also, the lion may fuse the input cues from its senses in locating prey). Hence, both motion and depth are considered important for predators.

The outer portion of the human retina, and other predators such as the eagle described above, has a much sparser population density of cone sensors and thus can be used to analyze daylight visual information more quickly using a process called pre-attentive vision. Once a depth or motion cue is detected, the eagle moves its fovea onto this area and uses the maximum visual acuity portion of its retina to identify whether the depth or motion cue was caused by an actual prey. This attentive vision processing of the foveal vision though is slower than the pre-attentive vision.

Humans use two distinct types of vision processes. However, humans are not always aware which one they are using at a particular time. The first type of processing is a whole scene interrogation that is termed a "soft focus" in some sports. This is commonly considered to employ "pre-attentive vision". The second type of processing is a highly fixated view of a portion of the scene in front of them. This highly fixated processing is commonly call "attentive vision" and is used to read signs, for example. What is not well known is that the pre-attentive vision process has a refresh rate that is five times faster than the attentive vision process.

The typical human vision refresh rate (the time required to produce a single mental image from the visual input of a person's foveal region, i.e., attentive vision process) is given as 200 milliseconds, and the stereopsis and depth perception has a limit around 20 arcsec, which is representative of the attentive vision processes. The pre-attentive temporal refresh rate, on the other hand, is typically given as between 25 and 32 Hz or approximately 40 milliseconds, which is five times faster than the attentive vision process. Processing speed is a very important aspect in the search and target acquisition/recognition process. To perform this task efficiently, humans must rely upon the pre-attentive vision process and not attentive vision.

The human vision processes have developed very sophisticated calibration techniques that occur without an awareness of their existence or implementation. That does not, however, mean that humans always have perfect vision and use the correct vision processes to address every vision problem encountered. Humans sometimes use intuition to solve vision problems and actually apply very inefficient methods for their solutions. There have been some attempts in the past to train pre-attentive vision without the knowledge of why the process works. Reading in general is performed as an attentive vision process where the foveal field of view at the typical reading distance of 60 cm has a width of approximately 2 cm. This allows even long words to be completed foveated (placed within the foveal field of view for identification). But humans are very familiar with the spelling of words and only recognition is needed to understand that a string of letters represents a particular word. In fact, humans can recognize strings of words without really identifying the individual words. This is the process that speed reading uses to increase the rate at which humans can derive the meaning from written text. What is not recognized by the users of this approach is that they are using pre-attentive vision that performs recognition vision processes five times faster than the foveal attentive vision identification process.

Based upon the foregoing understanding relating to pre-attentive vision, it is desirable to develop a vision training techniques which improve upon one's ability to utilize pre-attentive vision in an effective manner. The notion, however, that human senses including vision can be trained or enhanced in not novel. For example, U.S. Pat. No. 4,405,920, for Enhancing the Perceptibility of Barely Perceptible Images, Naomi Weisstein, Inventor, issued in 1983, discusses the use of a computer program to enhance visionary perception of faint images. Additionally, U.S. Pat. No. 5,088,810, for Vision Training Method and Apparatus, Stephen Galanter and Barry Milis, inventors, issued in 1992, involves different types of computer generated therapeutic eye exercise routines to increase performance. U.S. Pat. No. 6,364,486, for Method and Apparatus for Training Visual Attention Capabilities of a Subject, Karlene K. Ball and Kristina K. Berg, inventors, issues in 2002, discloses the use of a computer algorithm to improve attention vision.

Attempts at visual training have been specifically applied in treating dyslexia. Dyslexia is a problem that is related to how the human eyes' imagery is processed. As recent as September 2002, U.S. Pat. No. 6,364,486, for Method and Apparatus for Treating Dyslexia, was issued to Alison Marie Lawson. The Lawson patent is based upon the theory that Dyslexia is the result of unstable focus in one eye. According to Lawson, Dyslexics do not appear to fully use their magnocellular pathways, which are the pathways used in the brain to process fast moving objects. Dyslexia, according to Lawson, can be improved by strengthening of the magnocellular visual pathways through repetition of eye exercises. Lawson, however, fails to understand the true root to the Dyslexics problem and therefore discloses an inefficient remedy to such problem. Dyslexia is a problem associated with the way in which the left or right ordering of numbers or letters is perceived using attentive vision. Pre-attentive vision in a Dyslexic is not affected. Unlike the method disclosed in the Lawson Patent, the present invention describes a method of training Dyslexics using pre-attentive vision to calibrate or correct the problems associated with attentive vision.

Vision training has also been used in relation to sports, specifically baseball players. In an article published in the 2002 edition of the magazine entitled "Coaching Management", David Hill the author, speaks of training baseball players to be better hitters through vision exercises. Mr. Hill relates on page 18 of his article, how important it is to a baseball player to be able to see the ball before it is hit. Notwithstanding the opinions of Mr. Hill, however, and as stated on page 171 of the book entitled "Keep Your Eye on the Ball", Robert G. Watts, A. Terry Bahill, W.H. Freeman and Company, 2000. tracking a baseball moving at 100 mph, would require head and eye rotations in excess of 1000 degrees per second; an impossibility. Looking at an object (i.e., keeping your eyes on the ball) is an identification process using attentive vision, and the batter already knows that he is supposed to hit a baseball. The actual task that is needed is to track the path of the baseball in order to be able to swing the bat at the right time and place to be able to solidly contact the ball. This is a search and target acquisition task and not an identification task (requiring attentive vision). So the batter really should not look at the baseball but, rather, the background instead. The batter must use pre-attentive vision instead of attentive vision that simply is not fast enough to be used to follow the fast moving object. The veracity of this observation is easy to justify by way of example. Jugglers who must simultaneously track several objects cannot possibly track all of the objects that are being juggled by looking at them. They look at the background past the objects and are thus able to use the fast response pre-attentive vision to track them all at the same time.

While the concept of sensory training may not be novel, none of the prior art mentioned above, recognizes the value of using pre-attentive sensory perceptions to enhance attentive vision. With this in mind, the proper vision or sensory process or sequence of processes must be applied if one wishes to optimize the performance of a task. Furthermore, it is known that human vision can be efficiently trained if it is routinely exposed to the proper visual input for performing the process required for a particular task. In fact, some vision defects can also be cured or mitigated by altering the visual input to the eyes or training the eyes with the proper visual input images. Use of other senses such as hearing, smell and touch can be uses to strengthen the foregoing. The present invention overcomes the shortcomings of the techniques discussed above and provides an effective and efficient vision and sensory training and testing technique.

SUMMARY OF THE INVENTION

It is, therefore, an object of the present invention to provide an efficient sensory training method. Other objects and advantages of the present invention will become apparent from the following detailed description when viewed in conjunction with the accompanying drawings, which set forth certain embodiments of the invention.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as the basis for the claims and as a basis for teaching one skilled in the art how to make and/or use the invention.

Figure 1:
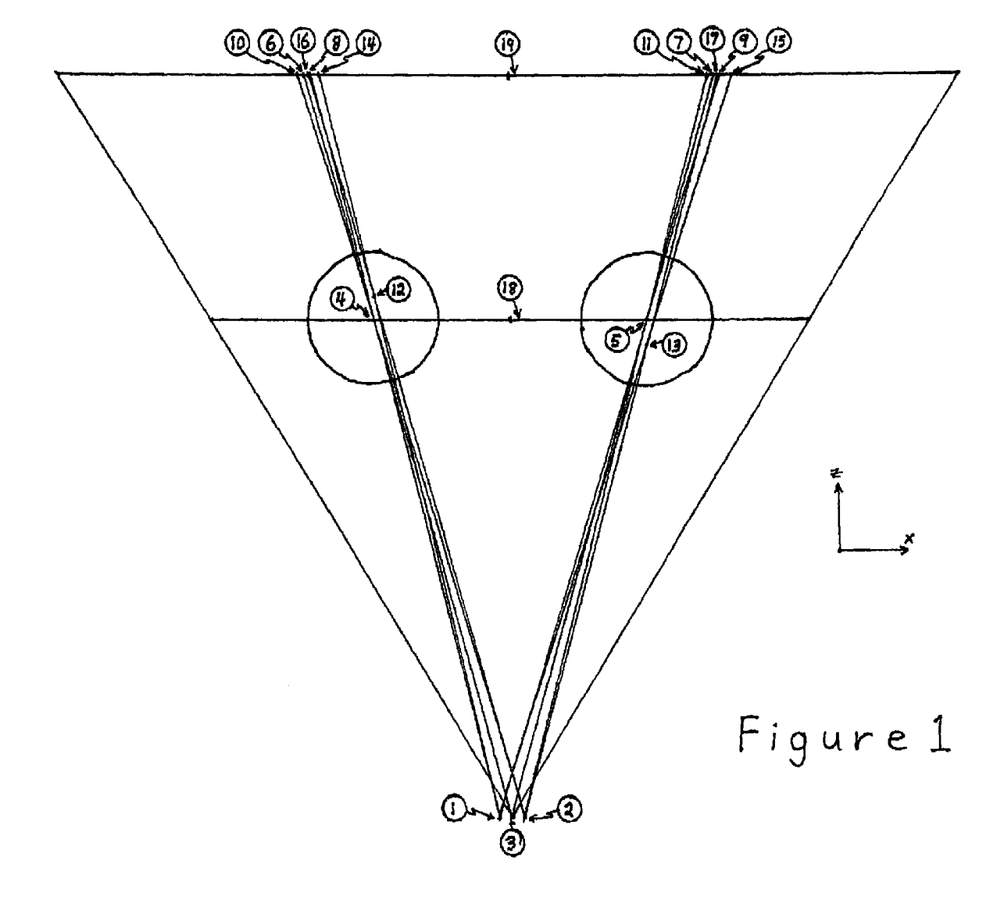
FIG. 1 is a schematic of a display used in accordance with a preferred embodiment of the present invention.

With reference to FIG. 1, a vision training system is disclosed which employs the use pre-attentive vision in enhancing the mental processes of subjects. In accordance with a preferred embodiment of the present invention, the process involves first creating a three-dimensional environment including at least two objects of shape, including a first object and a second object, situated in front of a background. The first object and the second object are spaced beyond the horizontal angular extent an individual is able to foveat using attentive vision. That is, the objects are spaced in a manner preventing an individual from using attentive vision to observe both objects simultaneously. The first object and the second object are further positioned to produce either motion cues, color cues and/or depth cues. Thereafter, the three dimensional environment is viewed by an individual and the response of an individual is studied to ascertain their ability to utilize pre-attentive viewing.

In accordance with a preferred embodiment of the present invention, the three dimensional environment is simulated on a two-dimensional display monitor. In addition, the horizontal angular extent required to prevent the use of attentive vision is 2 degrees of the entire width field viewed by the individual and the first object and the second object are positioned to produce depth cues by varying the depth range difference between the first object and the second object. In addition to the use of depth cues and motion cues, the textural contrast between the background and the first and second objects is varied to optimize the use of pre-attentive vision and/or enhance the testing process. Textural contrast is altered by varying color composition, edge fidelity, noise and intensity.

As discussed above, human vision is often characterized only for the attentive vision process. The temporal refresh for attentive vision as mentioned above is generally regarded to be approximately 200 msec, and the stereopsis and depth perception has a limit around 20 arsec. In contrast, and as discussed above, the pre-attentive temporal refresh rate is generally considered to be approximately 40 msec, which is five times faster than the attentive vision. The pre-attentive depth perception limit is approximately 3 arcmin at a nominal 10-degree separation, which is less sensitive than the attentive vision as measured for the central foveal vision.

The visual input for measuring and training human pre-attentive vision in accordance with a preferred embodiment of the present invention will now be detailed. Both depth and motion cues are determined through the fusion of the backgrounds viewed by both the left and right eyes. This is sometimes referred to as "stereoscopic fusion". This stereoscopic fusion is accomplished nearly instantaneously by our two eyes based on coarse spatial structure and shading features that represent more or less a vertical surface at a distance as seen from two lines of sight with horizontal angular separation (that is, left and right eyes which are horizontally separated).

In accordance with a preferred embodiment of the present invention, two objects of shape relating to the task of interest are used. Spheres, for example, can be used for baseball players. The two objects of shape are placed in the 3-dimensional (3-D) scene representation using a computer aided design (CAD) program such that they are approximately ⅔ of the distance to the background and are positioned with horizontal separation.

With reference to FIG. 1, and in accordance with a preferred embodiment of the present invention, a typical display would be a 43-cm monitor having approximately a 33-cm width that represents a 20-degree width field of view when the monitor is viewed from a distance to of 90 cm. A human can foveate approximately 10 percent of the horizontal angular extent of such a display or 2 degrees of the entire width field viewed by the subject. In order to force the observer to use pre-attentive vision rather than attentive vision, the spheres' closest edges must be separated by more than the 2-degree foveal extent (that is, 3.2 cm at 90-cm viewing distance).

In accordance with a preferred embodiment of the present invention, a typical scene would contain two 5-cm diameter spheres positioned with their centers located 9 cm from each side of the display. This produces a 10-cm separation between the inside edges of the two spheres. The diameter of the sphere is such that it is larger than the angular extent of the foveal vision and allows the spheres to be textured with coarse, medium, and fine spatial structure as used with attentive vision processes. Spatial structure can be explained by example. In a scene of a dining room, the large objects like the table, chairs and people would represent low frequencies. The plates on the table and the people's heads and limbs would represent medium frequency objects. The utensils, the people's fingers and designs on the plates would represent the high frequency or fine detail objects.

The 6.5-cm separation between the outer edges of the spheres and the outer edges of the respective right and left background edges of the display, prevent attentive vision from relating the edge of the background to the sphere's location in the background. In general, the size of the spheres and the spacing of the spheres substantially prevent the use of attentive vision for performing the depth determination task.

When employing the configuration described above, the background for the 3-D volume space (as defined and simulated within the two dimensional space of the display) could be situated as an xy-plane at a range of 1500 units in the z-direction from where the viewing takes place. If x represents the horizontal dimension, then the viewing locations for forming the stereo pair images will be plus and minus 7.5 units from z=0. This gives 10-mrad angular separation for the 1500-unit range for the background. The two spheres are positioned around a range of z=1000 with x positions of plus and minus 83.33 units that corresponds to an angular separation of 9.46-degrees between the centers of the spheres or a projected separation of 250 units at the background range of z=1500 units. For measurement purposes, the spheres are positioned at 25-unit intervals closer and farther than the 1000 nominal z-axis value. If the left sphere is positioned farther away (say 1025) then the right sphere is positioned closer (correspondingly at 975). The size of the spheres must also be changed with their range positioning to maintain their relative size of 83.33 unit diameters at a z-axis range of 1000 units. The sphere at 1025 z-axis range would have a diameter of 85.42 units, and the sphere at 975 range would have a diameter of 81.30. All of these spheres have the same projected diameter of 125 units at the 1500-unit background range.

At this point it is instructive to gain a perspective of how sensitive human depth perception resolution is compared to that of the 43-cm monitor with 1024×768 pixel resolution. At a viewing distance of 90 cm each pixel has approximately a 70-arcsec width. For the attentive vision stereopsis limit of 20 arcsec, this would imply that a shift of only 2/7 of a pixel is needed to be able to see the depth difference between two surfaces at a viewing range of 90-cm or a one pixel offset for a viewing range of 3.15 m.

The pre-attentive vision depth perception limit for objects separated by a few foveal regions is about an order of magnitude less sensitive that the attentive vision because there are about 60,000 cones in the foveal region out of about 6.5 million in the entire retina. There are about 100 times as many cones outside the foveal region covering an area nearly 10,000 times larger than the foveal region. Hence, the cone density is an order of magnitude less in each direction. As a result, the required display spatial resolution is less when training and/or testing pre-attentive vision as compared with attentive vision. This allows for a viewing range of 90 cm provided that CAD modeled images used are at least 512×512 pixel resolution. In accordance with a preferred embodiment of the present invention, the 512×512 resolution image can be used for fast Fourier transform (FFT) analysis of the image spatial frequency content but would have to be cropped (⅛ off the top and ⅛ off the bottom) to 512×384 before being imported into a PowerPoint display and expanded to the 1024×768 pixel monitor display.

In terms of the requirements of measuring the 3-arcmin pre-attentive depth perception limit for the 10-degree object separation at a viewing range of 90 cm, an offset of the objects' centers of 2 to 3 pixels at the 1024×768 pixel display or 1 to 2 elements at the 512×384 model resolution is needed.

The positioning requirements that this imposes for the CAD 3-D scene model generator for use in training and testing in accordance with the present invention are shown in FIG. 1. This is a y-axis, or top down view, of the objects, background, and camera positions in the xz-plane. The scale in the two axial directions as shown in FIG. 1 are different to permit viewing of the small detail of the extrapolated sphere centers in the background xy-plane. The x-axis scale is ratio is 3:10. It should be noted that the two spheres are shown as circles even though the z-axis projections are not to scale. The left [1] and right [2] camera positions (representing the human subject's left and right eye viewing locations) are equally spaced around the central scene origin [3] at (0,0). The separation between the left camera [1] position (−7.5, 0) and the right camera [2] position (+7.5,0) is 15 units in the x-a The two spheres of diameter 83.33 units have their centers positioned at a z-range of 1000 units. The left sphere center [4] is located at (−83.33, 1000). The right sphere center [5] is located at (+83.33, 1000). The projection of the left sphere onto the background plane at a range of z=1500[6] is positioned at (−125, 1500); the right sphere center projection [7] is positioned at (+125, 1500). The two sphere centers thus have again a separation of 250 units that at a range of 1500 units represents an angular separation of 9.46 degrees. For the left camera, the left sphere center projection in the background plane [8] is positioned at (−121.25, 1500) while the right sphere center projection [9] is positioned at (+128.75, 1500). The two spheres have again a separation of 250 units at the background range. For the right camera, the left sphere center projection in the background plane [10] is positioned at (−128.75, 1500) while the right sphere center projection [11] is positioned at (+121.25, 1500). Yet again the two spheres have a separation of 250 units at the background range.

Human pre-attentive depth perception will not be able to discern any difference in the range of the two spheres because the parallax is the same magnitude for both. If the left sphere center is moved 50 units further away to the position [12] located at (−83.33, 1050) and the right sphere center is moved 50 units closer to the position [13] located at (+83.33, 950), then there is a 100-unit difference in depth between them. The left camera now has a new left sphere center projection [14] of (−115.83, 1500) against the background and a new right sphere center projection [15] of (+135.92, 1500), or a separation distance of 251.75 units. The right camera now has a new left sphere center projection [16] of (−122.26, 1500) against the background and a new right sphere center projection [17] of (+127.24, 1500), or a separation distance of 249.50 units. There is thus a 2.25-unit difference in the parallax separations between the sphere centers against the background. The 20-degree field of view of the scene has an x-axis extent [18] of 364 units at the 1000-unit range in the z-direction and an x-axis extent [19] of 546 units at the 1500-unit range in the z-direction. Hence, the parallax difference of the spheres against the background is 2.25 units or 5.2 arcmin, which is just larger than the 3 arcmin pre-attentive vision depth perception limit. Hence, sphere center positions of z-axis ranges of 900, 925, 950, 975, 1025, 1050, 1075, and 1100 are used to produce range differences between the left and right sphere centers of 50, 100, 150, and 200 units. The 50-unit difference case has a parallax difference of 2.6 arcmin, which is less than 3-arcmin limit. As such, by varying the range differences one is able to train individuals to effectively use pre-attentive vision. To avoid problems of pixel value extrapolation, the background could be moved to a range of 1406.7 units where the x-axis extent would be exactly 512 units, or the angular extent could be reduced to 512 units at the 1500 z-axis range, which would represent and 18.85-degree width.

If more precise measurement of the pre-attentive vision depth perception is needed, the CAD 3-D model could be used to produce 1024×1024 pixel images that can be cropped to 1024×768 pixel images for display. Even with this though, it is not possible to obtain sufficient precision in the measurement of the pre-attentive vision depth perception limit by simply finer resolution adjustments of the sphere centers z-axis separation because of the pixel value extrapolation errors that occur. The measurement precision must, therefore, be derived by varying the parameters that impact the human vision derivation of the pre-attentive vision depth.

The actual measurement of the pre-attentive vision depth perception limit is dependent upon the difference of the texture contrast between the sphere and the background. This contrast difference for daytime vision is determined using the eyes' cone sensors since the rod sensors are used for low light, level vision. Parameters that influence this contrast include: textural spatial frequency, color composition, edge fidelity, noise, and intensity. The intent in accordance with a preferred embodiment of the present invention is to use a set of these parameters that can be varied to produce a range of contrast differences that will vary the measured value of the preattentive depth perception for the scenes generated with a fixed set of separation ranges between the two objects used to obtain more or less a continuum of difficulties for the range separations chosen.

Of the variables, the one with the least control between subjects is the intensity. Hence, the intensity is simply set to be bright enough to see the images comfortably. The next problem area arises with respect to edge fidelity and noise. Sphere edges with essentially step function transitions are least susceptible to the effects of noise. As will be seen below to be effective for color contrast variation there must be significant levels of noise randomly applied to single color scene layers to produce colored backgrounds. This results because the CAD 3-D model produces grayscale and not color images. Hence, the edges of all of the textures used will be high contrast with sharp edge transitions. The parameters that will be used to produce variability in the pre-attentive depth perception measurement and training are textural spatial frequency, color composition, and noise.

The textural spatial frequency will be discussed first. The texture of the background must be selected. A sharp edged pitted structure is a reasonable choice since there are a lot of multi-edged surfaces that can be made shiny. If several illumination sources are used in the simulation, many multifaceted light and dark patches are produced. The coarseness of the texture must be selected to provide a reasonable number of 4–6 cycle frequency patches over the 512×512 model spatial resolution. This low frequency content is needed in the background so that it will not be completely destroyed even by the largest levels of noise used.

The texturing of the sphere surfaces will now be discussed. The spheres have a projected diameter extent of 125 units at the background z-range. Three levels of spatial frequency content are chosen—low, medium, and high. For the 125-unit extent these could be represented by 1.5–3 cycles (low), 7–12 cycles (medium), and 20–50 cycles Sigh). In terms of the whole scene extent these would be 6–12 cycles (low), 30–50 cycles (medium), and 80–200 cycles (high). The actual textures could be periodic like a checkered pattern but should not be oriented vertically and horizontally. In addition, both spheres should not have the same orientation. Also, two periodic patterns should not be selected that produce pronounced beat frequencies. Hence, random structured textures are preferred, but care must be taken that in forming mid-range overall intensity the spatial frequency range is maintained.

One final note should be stressed in terms of the placement of illumination sources used in the simulation. The spheres must not cast recognizable characteristic elliptical shadows on the background.

The next parameter to be discussed is the use of color. The simplest choice is the primary colors (red, green, and blue) that correspond to the peaks of the human eye's cone sensors. Most CAD 3-D models produce grayscale texture patterns instead of multi-color texture patterns on the spheres. In accordance with a preferred embodiment, only one of the three texture patterns is used at a time and only one of the primary colors is used. The other two colors can be separately used on the remaining two patterns. In accordance with a further embodiment, a composite image can be formed by merging all three colored texture patterns to produce a multi-colored pair of spheres. The background, however, would remain as a grayscale because it is composed of equal amounts of the primary colors on the same texture pattern.

The issue of the grayscale representation of the background is not really a problem when the noise is added. As mentioned before, it takes a large noise level to destroy the edge content of step function edges. To produce multi-colored noise, random Gaussian noise is added to the separate texture pattern sphere images before they are colored. The images are digitized to 256-bit grayscale resolution. The individual images are contrast enhanced to produce many edges with the maximum grayscale difference. In order to destroy the edges of the images the noise must have a standard deviation that is on the order of, or larger than, this grayscale contrast difference. Three noise levels are thus chosen to accomplish this to varying degrees. The standard deviations for the Gaussian noise are 240, 360, and 480. Under the strongest noise, only a few percent of the background edge pixels are unaltered, yet the low frequency structure is still preserved because in stereo viewing only correlated components are retained and uncorrelated noise is discarded in the final representation of the scene content.

The final issue to be dealt with in the construction of the measurement and test images for pre-attentive depth perception is the background positioning. The background must be presented with several variations so that characteristic features or edges cannot be used with attentive vision to determine the depth of the individual spheres, especially when the test is given repeated for training purposes. A typical set of measuring or training images would be a random ordering of scenes of permutations of the variable parameters. There are eight different range scenes, six different color-texture patterns, and three different noise levels. Thus there would be 144 different scenes in the test. These images should be viewed at a fairly rapid pace to reduce the tendency of the observer to use attentive vision since the pre-attentive depth perception is determined very quickly once the stereo images are fused. Several different orderings of these 144 scenes can be produced for non-repetitive training purposes. There are many applications for this pre-attentive vision measurement and training including: any sport where a fast moving object is tracked, navigation of vehicles or aircraft, improved speed reading, and post operative training for lasik surgery patients.

If used to improve a baseball player's pre-attentive depth perception, the addition of an audio signal could enhance the player's application of their pre-attentive skill relating to hitting. An object tracker could be used to track the path of a pitched ball. A sound could be produced that represents the range of the ball to the batter's strike zone over home plate. As the ball approaches close to the strike zone, the pitch and/or volume level of sound could be increased until the ball finally reaches the strike zone at which time a definite noise could be made to represent that the pitch was a strike and should be contacted by the batter with his/her swing. If the pitch was not in the strike zone, no special sound would be made. Repeated training would allow the batter to use his hearing to hone the visual tracking skills needed to improve his batting percentage.

As discussed in the Background of the Invention, it is believed that measurement and training in accordance with the present invention can also be applied to some attentive vision problems, such as, dyslexia. The present invention applies pre-attentive vision training and testing in helping people overcome the problems associated with dyslexia. Reading, and in particular visual training to overcome dyslexia, is performed in an environment where the printed words or numbers are typically grayscale images that have no depth or color variations present for calibration. The key to proper training for the patient with dyslexia is to present letters and/or numbers in a display where pre-attentive vision is used to determine the ordering.

More particularly, and in accordance with a preferred embodiment of the present invention, Windows' Paint, a computer application providing for desktop publishing, can used to produce a grid of random letters. By way of example, if 12-point bold capital letters are used with basically five spaces (letters like "W" require less and "I" requires more) between letter and two-line spacing, a 20 wide by 12 high array can be produced. This can be displayed using Power-Point similar to the scheme used for the training and testing of pre-attentive vision described above but such that the width represents a 10-degree extent. Under these conditions there will be four or five consecutive letters in a line within the foveal region. The letter grid pattern can have letters removed to produce word size groupings or left as a complete rectangular grid. This array can be presented to both eyes either with black letters on a white background or white letters on a black background to determine the subject's degree of dyslexia in identifying the order of the letters by reading the first line left to right and the second line right to left, etc.

This test can also be performed using primary color lettering where the entire grid letters are either red, green, or blue against either white or black background. To calibrate out the problem of dyslexia requires that the left and right grid letters have a color-depth ordering in the pre-attentive vision. This is accomplished by producing a grid with letters in a pattern that have been offset to produce different depths that have different colors assigned to them. For example, if the evenly spaced set of grid letters is viewed by the right eye in a cross eyed stereo pair, the spacing of the left eye letters in the grid can be changed to produce peaks and troughs. The peaks are produced by shifting the letters one space to the right. For any particular letter this is accomplished by moving one of the spaces on the right side of the letter to the left side of the letter. This changes just that one letter with respect to the rest of the grid. It appears closer than the other letters. This process can be applied to the first letter and every third letter after it on the first line, the second letter of the second line and every third letter after it on the second line, the third letter of the third line and every third letter after it on the third line, and the first letter of the fourth line . . . , etc. This produces diagonal peaks in the letter grid that move from left to right down the grid.

The middle depth region of the grid is produced by leaving the letters directly right of the peak letters or two letters to the left of the peak letters alone. The troughs are produced by shifting the remaining letters one space to the left using the same process that was applied to the peak letters to shift them one space to the right. This produces a letter grid that has both peaks and troughs that proceed diagonally from the left to the right down the grid. The peaks can be colored with one of the primary colors, the middle letters with a second primary color, and the troughs with the third primary color. The background for the color can be either white or black. For initial training, the black background provides a more pronounced image because the individual cone sensors will only be receiving information from one depth plane.

When the subject views this color-depth grid of letters, their pre-attentive vision will counter any switching of the letter ordering derived by the foveal vision. By switching back and forth between attentive and pre-attentive vision the patient can train their foveal vision process to derive the correct letter ordering for the color-depth letter grid.

As the subject's training progresses, the color or depth aspect to the grid can be eliminated and white can be used instead of black for the background. In addition, different color-depth patterns can be used. The peak to trough sequence could be reversed or the diagonal shift could be from right to left going down the grid. The depth pattern could be changed to be a wave instead of a saw-tooth pattern, etc. In any case, the order of the letters must be random and different for each color-depth letter grid when the grid pattern is read from left to right and then right to left.

Patterns can also be produced that have actual words whose reverse spelling is a different word. In this case the grid pattern should be read only from left to right. The presentation mechanism for the display of the stereo images is not as restrictive as for the pre-attentive vision since the shape content is very distinct and not degraded by texture composition or noise. Hence, even a slide viewer type display could be used for administering the training.

The benefits and procedures associated with the use of the present invention in treating dyslexia will now be demonstrated with reference to the following example:

EXAMPLE

Background:

In accordance with Disclosure Document Number 518,460, Watkins, Jessica Rae Watkins ("Watkins") developed and administered a stereoscopic color-coded and depth-perception-based testing and training program to three patients from Dr. Radenovich's Children's Vision Center in December of 2002, using equilateral triangles with four different orientations. The results of this experiment were that of the three subjects thought to have dyslexic-like behavior, one did not show any difficulty in orientation determination throughout the entire program of testing and training; but, the other two exhibited severe problems with orientation determination during the baseline test and struggled throughout the training program. These two subjects, however, did not exhibit any orientation determination difficulty during the final testing. Discussions between Dr. Anthony Fierro of the Region 19 reading program and Watkins indicated that the next step in validating the procedure used to treat dyslexia was to perform a control group experiment.

Objective:

To perform an experiment using students diagnosed as having dyslexia and not having dyslexia. These students were all given a traditional baseline test to determine their level of difficulty in performing a visual orientation determination task. They were divided into two groups based on their scores and were fist given either the stereoscopic training or placebo training. They were all given a second orientation determination test to determine any change caused by the training given. They were then given the training they did not receive first and were again tested for orientation determination to determine any change following the second training.

Rationale:

What is currently thought to be the defining criteria for a person with dyslexia is their inability to associate a particular letter symbol with a particular sound or phoneme. Researchers in the area of treating dyslexia do not believe that dyslexia is caused by a vision problem since there are dyslexics who have 20—20 vision This test will demonstrate disagreement with the foregoing and further that dyslexia could in fact be the result of the human foveal vision being un-calibrated in terms of orientation determination. It is believed that when a person with dyslexia uses their foveal vision to identify letter or number symbols they do not see the same symbol orientated in the same direction each time they try to identify it.

This cause for dyslexia can be used to explain all of the symptoms of dyslexia, which includes the inability of a person to associate a particular letter symbol with a particular sound or phoneme. The biomimicking algorithm described in Disclosure Document 518,460 explains how predators with two forward looking eyes (this includes humans) perform visual search, target acquisition, recognition, and identification processes. One of the applications is the method that was used in this study as a potential cure for dyslexia. In essence, humans use two distinct forms of vision. The first is a whole scene view of the world around us. This is accomplished using what is called pre-attentive vision. Our pre-attentive vision occurs automatically without having to think about it. This vision process is used to locate food and danger. It is also used for navigating. The visual process elements that are used in this locating process are called cues. The primary visual cues used in pre-attentive vision are motion, depth and color. These cues allow us to locate possible food and danger and allow us to reposition the central portion of our eyes (the fovea) on the object to be identified. The foveal vision is then used to identify the object located by the pre-attentive vision using a process called attentive vision. Problems with reading can occur because reading skips the pre-attentive vision phase and jumps straight to the attentive vision process. Reading is not an automatic human function but rather is a learned skill.

The format for reading text is black letters on a flat white background. If an individual's foveal vision is calibrated correctly for orientation determination, there is no problem learning to read if the individual has normal vision. But, if the connections of the very small foveal region in our eyes' retinas (a 0.5 mm diameter circle with 60,000 color cone sensors) are not correctly channeled to the back portions of our brains that perform the complex mental processing that produces the single picture we derive from our two eyes, the images of letters that are seen many not have the proper orientation. In fact, the letters may have random orientations each time they are viewed. The key to correcting the problem would then be to calibrate the foveal vision in terms of orientation determination. That is exactly the approach taken in this study. This is accomplished by using by using a symbol grid that contains depth and color cues that can be used by both pre-attentive and attentive vision to allow the attentive vision to be calibrated for orientation determination by transitioning the correctly determined orientation of the pre-attentive vision to the attentive vision of the foveal region.

Figure 2:
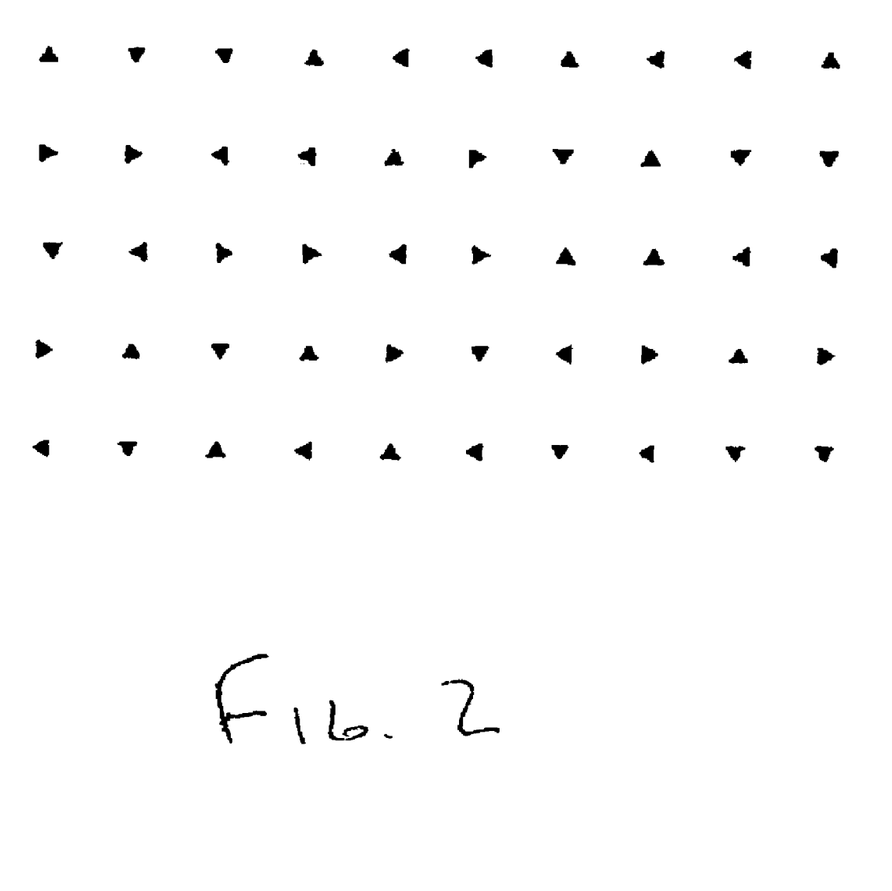
FIG. 2 is a display used in treating dyslexia in accordance with the present invention.

Orientation Determination Test:

Since it is symbol orientation determination and not letter identification that is important, only triangles are used instead of any letters. The baseline test consists of five rows of ten triangles that have one of four random orientations. The triangles point directly toward one of the four random directions—up, down, left or right. A representation of this test is shown in FIG. 2. This depiction is with black triangles on a white background whereas the actual test that was displayed on two computer monitors that were viewed with opposite eyes simultaneously had white triangles on a black background.

There were also two equivalent tests that were given after completion of each of the two training programs—the foveal vision orientation calibration and the placebo.

The foveal vision orientation calibration training program consisted of five sessions given on different days. They were stereoscopic displays where color and depth were added to the symbol grids to allow the preattentive vision to lock the symbol grid in space and transfer this orientation information to the foveal vision for calibrating its orientation. The task performed by the subject was slowly transitioned from a primarily pre-attentive vision task to a solely attentive vision task of orientation identification to accomplish the calibration of the foveal vision.

The placebo training program used the two-computer-viewing setup but did not contain any depth or color cues for determining orientation. The test consisted of the letters "b", "d", "p", and the vowels. The purpose was to see if simple three letter words with vowels as the second letter could be properly identified and pronounced when they were hidden in a letter jumble line of ten of the same letters per line. There were five words in each testing session and five letter jumble lines with one of the words hidden in each line. The task that was given was to find at most one of the words in each line. The subjects were timed in hopes of improving their concentration. The subjects were shown each of the five words several times with different colored print by computer display just prior to testing. They were given a printed sheet with the words to look at during the test.

One of these tests is shown in Table 1. The words "bad, bed, bid, bod, and bud" are hidden in the five lines.

TABLE 1

Placebo letter jumble test for bad, bed, bid bod, and bud.

| d | a | b | p | e | b | u | d | o | b |
| o | d | e | b | i | d | a | b | u | p |
| d | i | b | u | p | o | b | e | d | a |
| b | u | p | a | b | o | d | i | b | e |
| e | b | a | d | i | p | o | d | u | b |

Results:

The results of the orientation determination testing are shown in Table 2. The subjects are listed as Group A or Group B. Group A received the calibration training first and then the placebo training. Group B received the placebo training first and the calibration training.

TABLE 2

Orientation Determination Test Results

|  | A-1 | A-2 | A-3 | B-1 | B-2 | B-3 |
|---|---|---|---|---|---|---|
| Test 1 | 8/0 | 4/1 | 1/0 | 10/0 | 2/4 | 3/0 |
| Test 2 | 0/0 | 0/0 | 0/0 | 12/0 | 0/2 | 25/0 |
| Test 3 | 0/0 | 0/0 | 0/0 | 0/2 | 0/0 | 0/0 |

The entries for the subjects for each test consist of the number of incorrect orientation determinations out of the fifty triangles followed by the number of determinations that were stated and then changed. As can be seen after the orientation training had been given, none of the subjects made any mistakes in orientation determination and only two reversals were made. In general, the subjects that received the placebo training first (Group B) did about the same on the second test except for subject B-3. This subject reversed every left and right orientation determination. The possible reason for this will be discussed after discussing the placebo test results.

The placebo test results are combined for the four tests taken in Table 3. There were 20 total words that could have been found, five from each test. The results are given as the number of correctly found and pronounced words followed by the number of words not found followed by the number of incorrect words pronounced by Group A that had received the orientation calibration training first. There was only one incorrect answer and that was a repeat of the word from the previous line. The subject may have looked at the word list and then looked at the wrong line and found the same word twice. Also of interest is the subject B-3 that had no trouble finding any of the words until the last test. This was the test shown in Table 1. The subject identified the last three letters of the sequence "dub" as "bud" and pronounced it as "bud". It is very interesting that this individual also reversed every left and right orientation identification in test 2 two days later. It is possible that this phenomenon could have been caused by allergies. It is not known if the orientation calibration has corrected this problem for the condition when the individual has allergy symptoms. Subject B-3 did not make any orientation determination mistakes in the final test.

TABLE 3

Placebo Letter Jumble Test Results

|  | A-1 | A-2 | A-3 | B-1 | B-2 | B-3 |
|---|---|---|---|---|---|---|
| 4 Tests | 15/5/0 | 19/0/1 | 19/1/0 | 8/0/12 | 18/1/1 | 19/0/1 |

In terms of improved letter identification and word pronunciation, subjects A-1 and B-1 will be compared. Both had difficulty with the first orientation determination test. Subject B-1 correctly found and pronounced only 8 out of 20 words in the placebo testing before having received the orientation calibration training. Of special note is the score for the test shown in Table 1. Only one of the words was correctly found and pronounced and four incorrect words were given. Upon completion of the final test, subject B-1 was given the last placebo session again. This time three words were correctly found. The first mistake was the word "bed" was given for "bid." The subject was asked to locate the word found in the letter jumble line and identified the letters "bid." The subject was asked to pronounce the word found and again said the word "bed." It appears that the ability to correctly identify letters has been accomplished, but the association of the correct phoneme with the identified letter still requires further training. The processed foveal vision is sent to the left side of the brain, and subjects with orientation determination difficulties will have to learn how to associate the correctly identified letters with the proper phonemes for use in the left side of the brain. To see how different the two vision processes are is possible by taking another look at the problem experienced by subject B-3. Before each test the subjects are shown in a large black card with a white triangle on it. They are shown the card orientation that represents the pointing of the triangle for up, down, left and right. After subject B-3 reversed every left and right triangle orientation determination on test 2 that have symbols so small that they can only be identified using attentive vision, the subject was asked to identify the orientation of the large triangle. The subject properly identified left and right that could be accomplished using pre-attentive vision because of the size of the triangle.

The subject could now use the sense of touch to reinforce their visual orientation skills. A set of cards with small letters (on the order of 0.6 cm in height for viewing from a distance of 40 cm) printed on each card and a black border to represent the bottoms are used. The subjects could be given single letters, multiple letters or words. A set of transparent disks with the same size letters printed on them is used. The subjects must choose the disks with the proper letters and orient them to exactly overlay the card letters. For each letter, the letter is identified and its sound spoken. If a word is used, the word is spoken after all its letters have been oriented and identified. The sense of touch is thus used to reinforce the visual orientation and letter identification task skill.

Other Testing:

There were two other vision tests that were give by Allen and Virginia Crane in conjunction with the orientation determination testing. The subjects were given an eye tracking test that included the reading of simple story and a set of ten questions associated with the content of the story while the subject's eye tracking was measured. They were then given a test of symbol identification speed (PAVE). There was a significant amount of data collected on the actual eye tracking during each reading but would take a significant amount of explanation to be fully understood. Instead only the reading comprehension and symbol identification speeds will be shown in Table 4.

TABLE 4

Eye Tracking and Reading Comprehension Testing

|  | A-1 | A-2 | A-3 | B-1 | B-2 | B-3 |
|---|---|---|---|---|---|---|
| Story 1 | 5/10 | 6/10 | 9/10 | 8/10 | 9/10 | 10/10 |
| Story 2 | 7/10 | 8/10 | 10/10 | 9/10 | 10/10 | 10/10 |
| Story 3 | 8/10 | 10/10 | 9/10 | 10/10 | 10/10 | 10/10 |
| PAVE 1 | 30 | 60 | 60 | 35 | 30 | 50 |
| PAVE 2 | 20 | 30 | 55 | 20 | 30 | 25 |
| PAVE 3 | 35 | 50 | 85 | 35 | 45 | 50 |

What is of note from Table 4 is the reading comprehension improvement for subjects A-1, A-2 and B-1. All of the subjects improved or maintained their comprehension level. Subject A-3 missed one question in each Story 1 and Story 3 but was reading at well above their grade level. There was a little problem with the PAVE results because the test was given differently the second and third times, which may have biased the first results that appear high. Even so, the speed at which all the subjects were able to identify a particular symbol increased dramatically between PAVE 2 and PAVE 3. The number refers to how many lines of three symbols were shown per minute and correctly counted. The three symbols were blinked onto the screen sequentially one after the other while the line was viable.

CONCLUSIONS

The results of this study were very positive. All of the subjects have improved their symbol identification capabilities with their now calibrated foveal vision. They now have the tools to correctly identify symbols such as letters and begin to associate the appropriate phonemes with these symbols using the left portion of their brains. Many of the subjects were not able to do this before the testing and training program. All of the subjects demonstrated improved concentration and eye coordination in reading with improved reading comprehension. For those subjects that are seeing the letter symbols with the correct orientation associated with them for the first time, it will take a little training to be able to associate the appropriate phoneme with the identified symbol using attentive vision and the left side of their brains before they will be able to read a their peers' level. This process however is much easier than the approach they have been using which is to use pre-attentive vision and their right side of their brains and transferring this information to the left side of the brains to be used with speech, spelling and language functions.

While the preferred embodiments have been shown and described, it will be understood that there is no intent to limit the invention by such disclosure, but rather, is intended to cover all modifications and alternate constructions falling within the spirit and scope of the invention as defined in the appended claims.

The invention claimed is:

1. A method for training or testing vision, comprising the following steps:
   creating a three-dimensional environment including at least two objects of shape, including a first object and a second object, situated before a background;
   wherein the space between any object is beyond the horizontal angular extent an individual is able to foveate using attentive vision;
   positioning the first object and the second object to produce either movement cues, color cues or depth cues; and
   viewing the first and second object with the left eye and the first and second object with the right eye using pre-attentive vision and studying the response of an individual thereto.

2. The method according to claim 1 wherein the horizontal angular extent between the first and second object is at least 2 degrees of the entire field width viewed by the individual.

3. The method according to claim 1, wherein the first and second object are positioned to produce depth cues by varying the depth range difference between the first object and the second object.

4. The method according to claim 1, further including the step of using an audible sound, unique smell or specific touch sensation to alert the individual to a correct response.

5. The method of claim 2, wherein the depth cues are provided within a range of the pre-attentive depth perception limit.

6. The method of claim 4, wherein the pre-attentive depth perception limit is approximately 3 arcmin.

7. The method of claim 2, further including the step of varying the textural contrast between the background and the first and second objects.

8. The method according to claim 6, wherein the step of varying includes varying textural spatial frequency.

9. The method of claim 6, wherein the step of varying includes varying color composition.

10. The method of claim 6, wherein the step of varying includes varying edge fidelity.

11. The method according to claim 6, wherein the step of varying includes varying electronic signal noise.

12. The method according to claim 1, further including the step of varying the textural contrast between the background and the first and second objects.

13. The method according to claim 1, wherein the background includes varying the textural positioning of features within said background.

14. The method according to claim 1, wherein the method is applied in the treatment of dyslexia.

15. The method of claim 13, wherein the step of studying includes creating, positioning and viewing to teach individuals to utilize pre-attentive vision in reading.

16. The method of claim 13, wherein pre-attentive vision is used to calibrate the attentive vision of the foveal region.

17. The method according to claim 13, wherein the first and second object are similarly shaped but orientated differently.

18. The method according to claim 13, wherein depth and color cues are applied.

* * * * *